United States Patent
Baugh

(10) Patent No.: US 6,472,161 B1
(45) Date of Patent: Oct. 29, 2002

(54) METHOD OF EVALUATING BLOOD CLOT LYSIS CONDITION

(76) Inventor: Robert F. Baugh, 7926 Windcrest Row, Parker, CO (US) 80134

( * ) Notice: Subject to any disclaimer, the term of this patent is extended or adjusted under 35 U.S.C. 154(b) by 0 days.

(21) Appl. No.: 08/583,761

(22) Filed: Jan. 11, 1996

Related U.S. Application Data

(63) Continuation of application No. 08/296,862, filed on Aug. 26, 1994, now abandoned, which is a continuation of application No. 07/962,900, filed on Oct. 15, 1992, now abandoned.

(51) Int. Cl.$^7$ ................................................. C12Q 1/56
(52) U.S. Cl. ........................................... 435/13; 436/69
(58) Field of Search ............................. 435/13; 436/55, 436/69

(56) References Cited

U.S. PATENT DOCUMENTS

| | | | |
|---|---|---|---|
| 3,302,452 A | | 2/1967 | Leslie |
| 3,307,392 A | * | 3/1967 | Owen et al. |
| 3,525,254 A | | 8/1970 | Milanes |
| 3,854,324 A | | 12/1974 | Altshuler et al. |
| 3,920,833 A | * | 11/1975 | Cook et al. .................. 424/303 |
| 3,963,349 A | | 6/1976 | Albright |
| 4,000,972 A | | 1/1977 | Braun |
| 4,026,671 A | | 5/1977 | Simons et al. |
| 4,040,788 A | | 8/1977 | Simons et al. |
| 4,058,367 A | | 11/1977 | Gilford |
| 4,074,971 A | | 2/1978 | Braun et al. |
| 4,081,242 A | | 3/1978 | Girolami |
| 4,131,549 A | * | 12/1978 | Ferrara ....................... 210/359 |
| 4,276,383 A | * | 6/1981 | Leighton et al. ............. 435/291 |
| 4,285,906 A | | 8/1981 | Meltzer et al. |
| 4,390,499 A | | 6/1983 | Curtis et al. |
| 4,391,780 A | | 7/1983 | Boris |
| 4,443,408 A | * | 4/1984 | Mintz .......................... 422/73 |
| 4,533,519 A | | 8/1985 | Baugh et al. |
| 4,534,939 A | | 8/1985 | Smith et al. |
| 4,551,308 A | | 11/1985 | Mintz |
| 4,599,219 A | | 7/1986 | Cooper et al. |
| 4,612,801 A | | 9/1986 | Girolami |
| 4,663,127 A | | 5/1987 | Jackson et al. |
| 4,671,939 A | | 6/1987 | Mintz |
| 4,752,449 A | | 6/1988 | Jackson et al. |
| 4,797,369 A | | 1/1989 | Mintz |
| 5,095,104 A | * | 3/1992 | Gordon ....................... 536/4.1 |
| 5,314,826 A | * | 5/1994 | Baugh .......................... 436/69 |

OTHER PUBLICATIONS

DiMinno et al (1989) Abstract Only, Pharmacol Res 21(2) 153–61.*
Kovacs et al (1990) Abstract Only, Angiology 41(10): 829–835.*
"Blood Component Therapy, A Physician's Handbook," American Association of Blood Banks, 1975.
J. Hirsh, M.D. and E. A. Brain, M.D., "*Hemostasis & Thrombosis, a Conceptual Approach*," Second Edition, pp. 1–45, 1983.

* cited by examiner

Primary Examiner—Ralph Gitomer
(74) Attorney, Agent, or Firm—Steven C. Petersen; Hogan & Hartson, LLP

(57) ABSTRACT

Blood is tested for clot lysis conditions such as natural lytic capabilities, the effect of previously administered thrombolytic and anti-thrombolytic agents, and dose responses thereto, by forming a clot in a sample of blood, lysing the clot, and measuring the elapsed time period from initial clot formation to clot lysis, all while continuously evaluating the blood sample. Thrombolytic agents include streptokinase, urokinase and recombinant tissue plasminogen activator. Plasmin and plasminogen activator inhibitors, clot activating agents (e.g. kaolin), and agents to deactivate anticoagulants (e.g. heparinase) may also be used as reagents during testing.

31 Claims, 7 Drawing Sheets

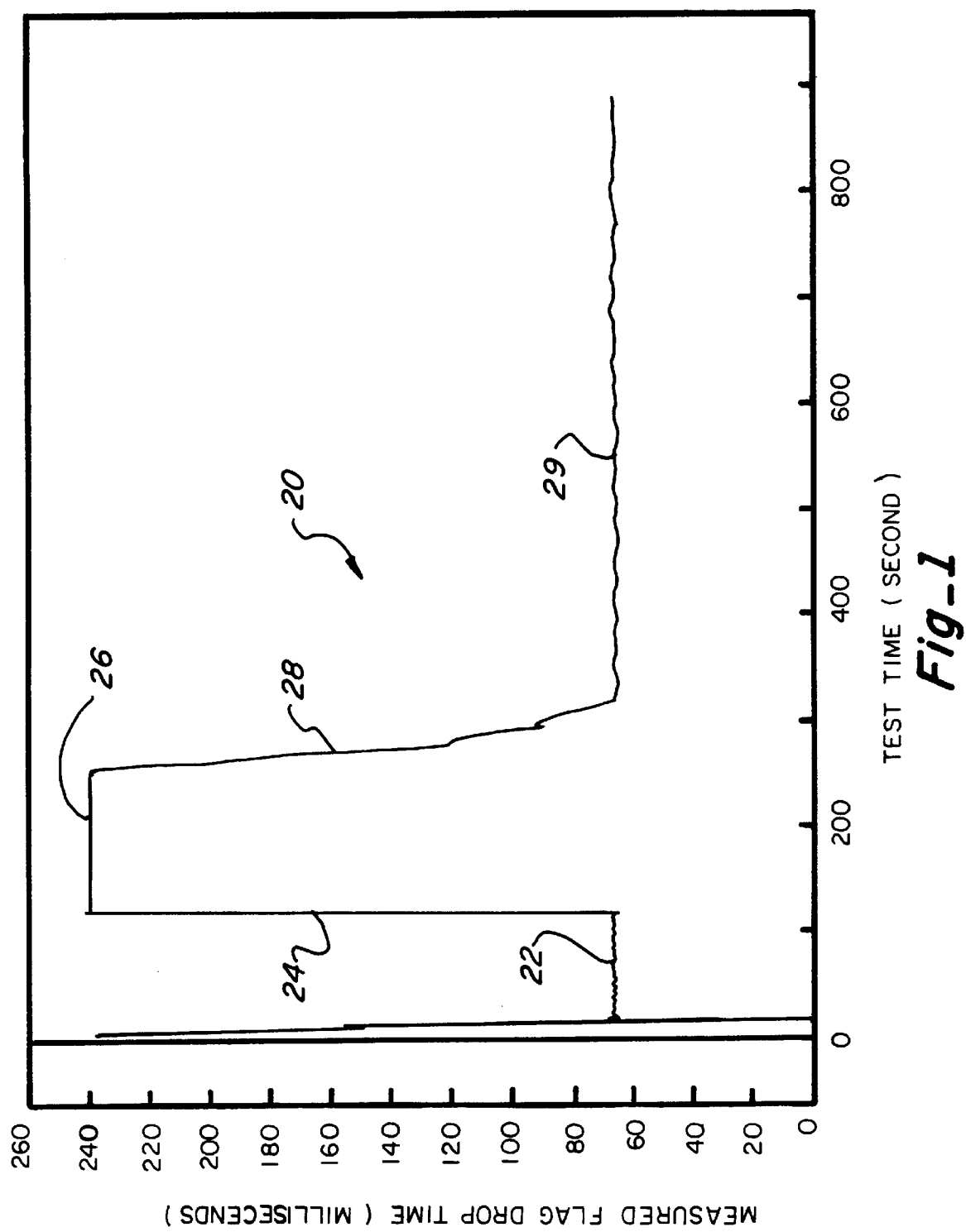
Fig_1

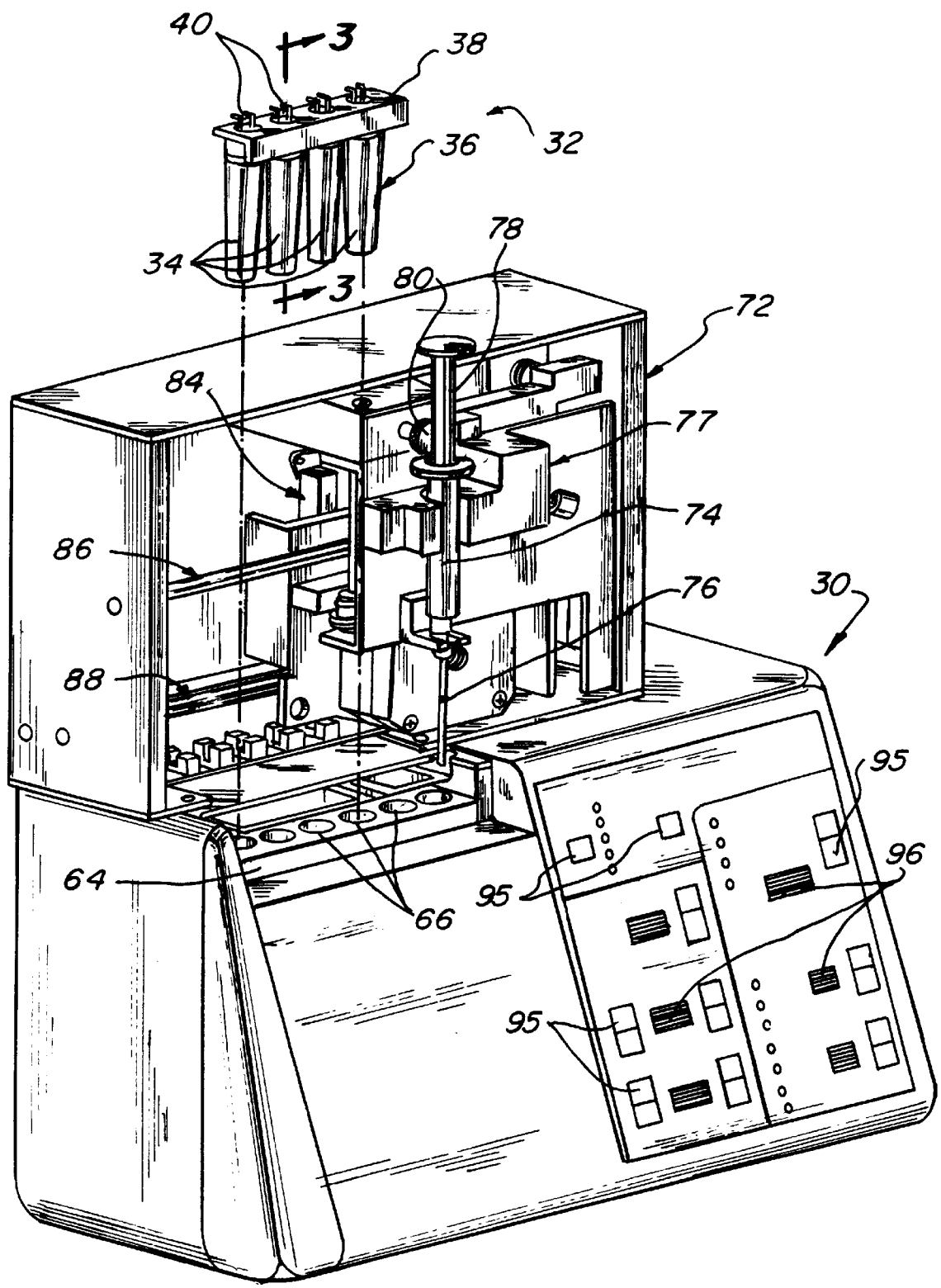
Fig_2

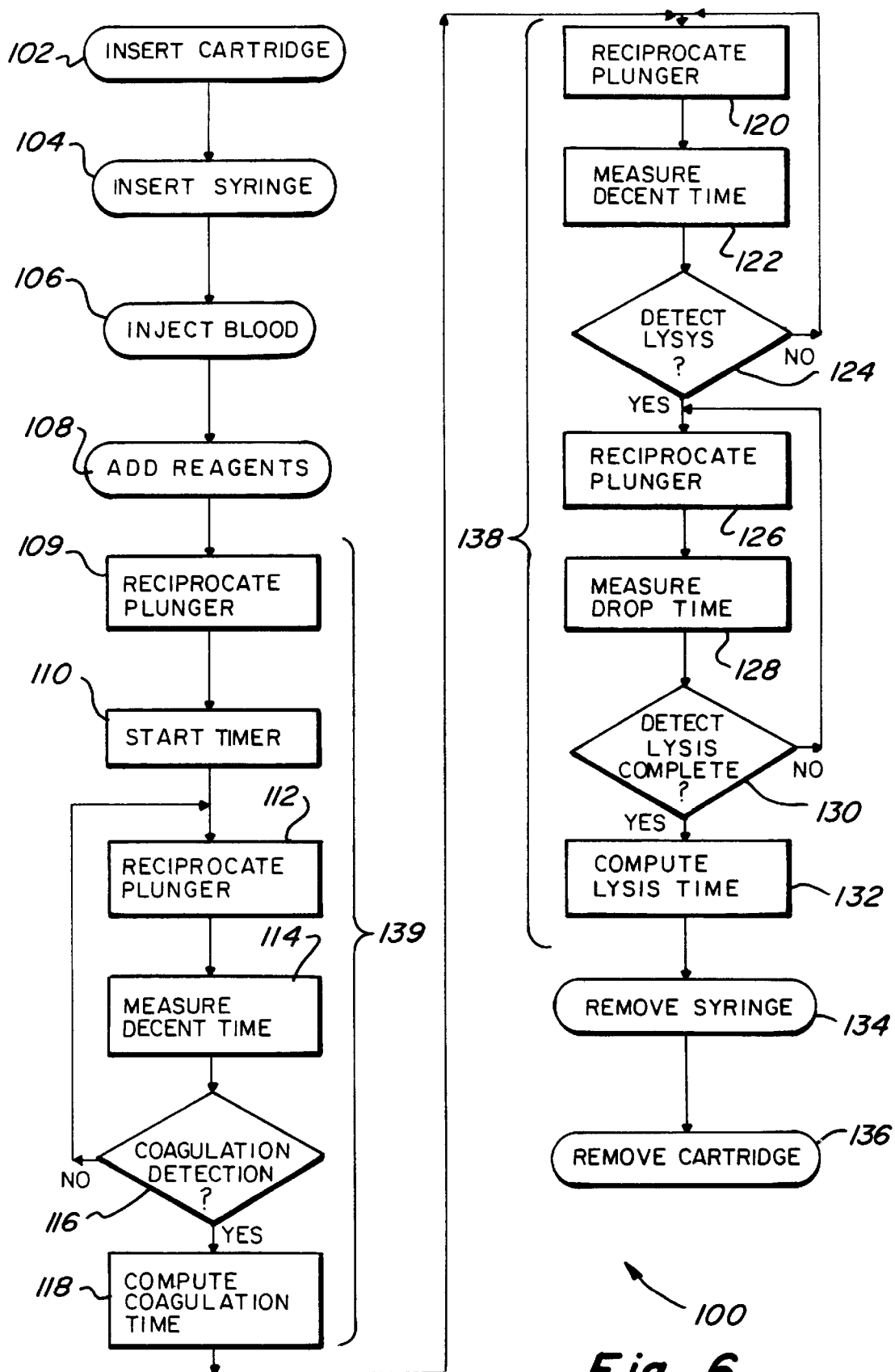
Fig_6

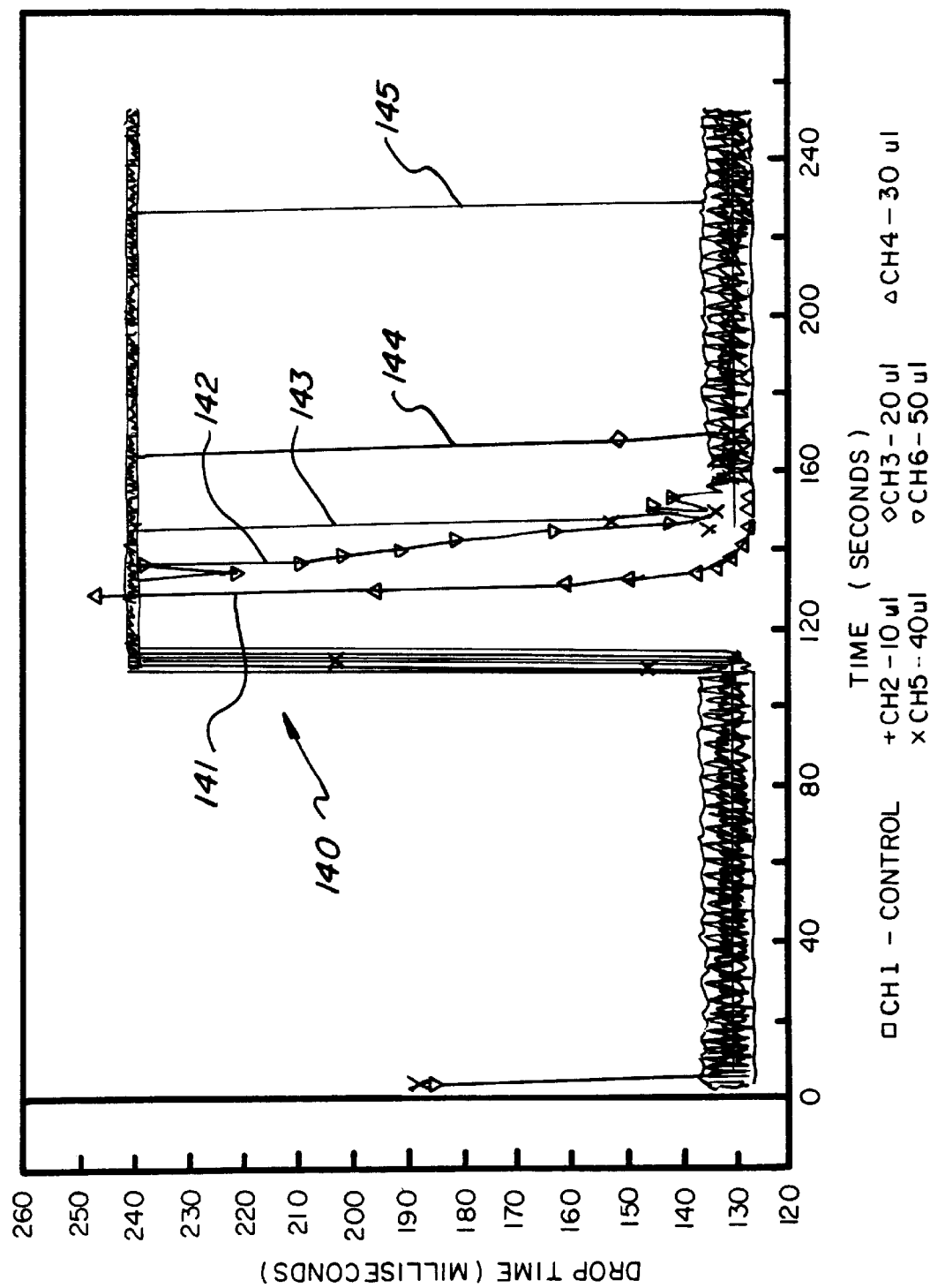
Fig_7

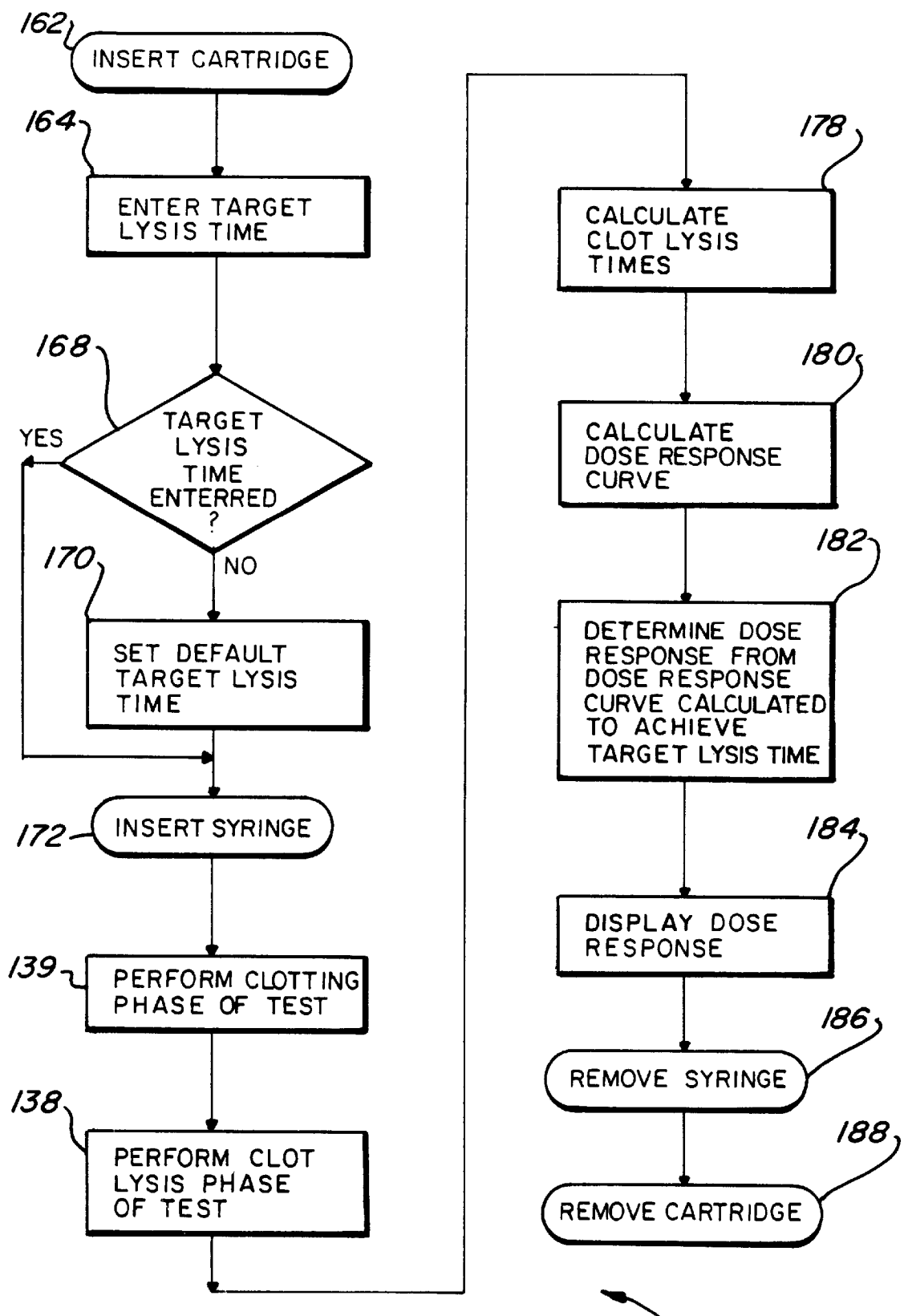
Fig_9

METHOD OF EVALUATING BLOOD CLOT LYSIS CONDITION

This application is a continuation of Ser. No. 08,296,862 filed Aug. 26, 1994, now abandoned which is a continuation of Ser. No. 07,962,900 filed Oct. 15, 1992 now abandoned.

CROSS REFERENCE TO RELATED APPLICATIONS

This is a continuation of application Ser. No. 07/962,900, filed Oct. 15, 1993, now abandoned.

This application is related to a U.S. patent application for Platelet Activation and Function Evaluation Technique, Ser. No. 749,211, filed Aug. 23, 1991 now abandoned, and to a U.S. patent application for Blood Clot Mass Measuring Technique, filed concurrently herewith, both of which are assigned to the assignee hereof and both of which are hereby incorporated herein by reference.

FIELD OF THE INVENTION

This invention relates to a technique for determining and measuring clotting related conditions in blood. More particularly, this invention relates to a new and improved technique for determining blood clot lysis conditions. In addition the present invention pertains to determining blood clot lysis times quickly and consistently with a high degree of sensitivity, to detecting thrombolysis or pathological fibrinolysis, to measuring the effect of therapeutically administered thrombolytic and anti-fibrinolytic agents, and to developing dose response information for the therapeutic administration of thrombolytic and anti-fibrinolytic agents, among other things.

BACKGROUND OF THE INVENTION

Fibrinolysis is the process in which blood clots are dissolved. Fibrinolysis is the final step in the natural reparative process which follows blood clot formation, as when a blood clot which was previously formed in response to blood vessel damage is subsequently dissolved after the damage has been repaired. Fibrinolysis may also be induced by the therapeutic administration of thrombolytic agents. Thrombolytic agents are administered to avoid the complications of pulmonary embolism resulting from lower limb venous thrombosis and to minimize the cell destruction of myocardial infarctions, gangrene and stroke caused by arterial thrombosis, among other reasons.

Whether or not cell destruction can be minimized after physiological events such as myocardial infarctions, stroke or gangrene may depend, in part, upon the existence of pathological or therapeutically induced thrombolysis. In order to eliminate or minimize such cell destruction in an individual who has undergone or is undergoing a stroke, heart attack or similar event, it would be helpful to ascertain quickly whether the individual's clot lysis ability is within a normal range of lytic response times. By comparing the individual's specific lytic response time to the average lytic response time of a normal, non-pathogenic individual, a treating physician could determine whether the patient's specific lytic response capability needs to be treated or otherwise taken into consideration.

Under conditions when arterial or venous thrombosis has occurred or is likely to occur, such as during and after surgery, it becomes critical that the treating physician have reliable information available about an individual's fibrinolytic processes. For example, clot formation is especially likely to occur during cardiac surgery utilizing extracorporeal passage of blood. Although clotting during cardiac surgery may be minimized through use of heparin or other anticoagulants, a surgical patient's natural lytic ability can help avoid surgical complications by dissolving any clots that form. If a particular surgical patient's lytic ability is impaired, a physician may administer thrombolytic agents to maintain a particular level of lytic activity and to avoid the possibility of permanent and disabling clot formation occurring during surgery. To maintain a desired level of lytic activity, it would be helpful to detect whether the administration of a thrombolytic agent had the desired effect upon the surgical patient.

It would be further helpful for treating physicians to be able to quickly and accurately monitor a patient's total lytic activity, i.e. lysis resulting from both natural fibrinolytic activity and physiological responses to the therapeutic administration of thrombolytic agents. It would also be helpful to be able to distinguish changes to properties of clotted blood caused by lytic activity from changes to properties of clotted blood caused by other therapeutically administered agents or by pathological or other conditions, such as, for example, changes related to disseminated intravascular coagulation. In order to monitor blood condition changes caused by lytic activity, a test which evaluates changes to a sample of clotted blood in which lysis is allowed to proceed and compares those changes with changes to a sample of clotted blood in which lysis is suppressed would prove useful. However, no such test is currently known to be available. Such a test might be based upon plasmin and plasminogen activity in the sample of blood. Plasminogen is a naturally occurring blood component and is a precursor of plasmin. Plasmin is an enzyme which degrades fibrin into soluble products. One way in which the body promotes fibrinolytic activity and in which thrombolytic agents increase lytic activity is by stimulating plasmin and plasminogen activators to cause the formation of plasmin from plasminogen. If an inhibitor of plasmin and plasminogen activators is added to a sample of blood, then the effects of previously administered thrombolytic agents and naturally stimulated fibrinolytic activity are suppressed. The addition of an inhibitor of plasmin and plasminogen allows the lytic activity to be monitored in such a way to evaluate the overall contribution to clot lysis from plasmin.

In addition to the current limitations on measuring the effect of therapeutically administered thrombolytic agents, physicians have been hampered by an inability to prescribe individualized doses of thrombolytic or anti-fibrinolytic agents tailored to the unique physiological responses of a particular patient. Currently, no known tests are commercially available to determine the dose response to thrombolytic and anti-fibrinolytic agents. In the absence of such dose response data, a standardized dose is usually prescribed. A standardized dose may be either inadequate or excessive for a particular patient because of variations in body size, blood volume, blood chemistry and pathological or surgical conditions.

Currently there are methods available to measure some characteristics of clot lysis, as exemplified by U.S. Pat. No. 4,276,383 to Leighton, et al. However, many prior art techniques are subject to certain technical problems. Generally, the known clot lysis measuring methods are expensive to perform, produce relatively inconsistent results, and are not suited to providing information responsive to real-time surgical or emergency conditions. Some of these prior methods tend to be cumbersome, such as when clots must be pre-formed under special conditions outside of the vessel or chamber in which clot lysis testing later occurs. These prior methods often require special collection and processing procedures, thus limiting the use of blood or plasma samples collected only for clot lysis testing. These prior methods are also susceptible to inconsistent results because they require sample mixing procedures which often involve repeated manual inversion or other manual manipulation of the testing chamber. Manual mixing can result in incomplete or variable mixing of the sample and reagents, resulting in either incomplete activation or deactivation of the components which would otherwise block or promote the clotting or lysing reactions to be measured.

It is against this background that the below described significant improvements and advancements have evolved in the field of measuring clotting- and lysing-related conditions in blood.

SUMMARY OF THE INVENTION

A significant aspect of the present invention relates to evaluating a clot lysis condition in a sample of blood. A clot is formed in the sample of blood and thereafter the clot is lysed. The time to lyse the clot relative to the time in which the clot was formed is measured to determine the lysis condition. By measuring the clot lysis relative to the clot formation, the information available from the clot lysis condition is more accurate and more directly related to actual conditions.

Other significant aspects of the invention relate to the types of tests which can be performed by evaluating the clot lysis condition. A test to determine the existence and effect of any previously administered thrombolytic agent in the sample of blood is achieved by testing two similar samples of blood. One sample contains an inhibitor of plasmin and plasminogen activator. The inhibitor inhibits the effects of therapeutically administered thrombolytic agent in the blood sample, and any difference in measured clot lysis times from the two samples indicates the existence of the previously administered thrombolytic agent which was not inhibited in the other sample. Another test is a dose response test to a thrombolytic agent, and a third test is a dose response test to an anti-thrombolytic agent. In both dose response tests, different concentrations of the thrombolytic or anti-thrombolytic agents are tested by measuring the lysis times of a plurality of different samples. The measured lysis times are correlated to the concentrations, and information is derived by which to predict dose responses. Furthermore, target lysis times may be selected, and information used to predict the concentration of a thrombolytic or anti-thrombolytic agent to be applied to achieve the target lysis time.

Another aspect of the invention relates to a test cell in which to perform the clot lysis condition. The clot formation and clot lysing are performed in a container or test cell into which the sample of blood and the reagents appropriate for evaluating the clot lysis condition have been added. The test cell includes a reagent chamber, a reaction chamber and a displaceable sealing member between the reagent and reaction chambers. The reagent chamber may contain a clot activating agent such as kaolin, an agent to deactivate anticoagulants such as heparinase, a thrombolytic agent such as streptokinase, urokinase and recombinant tissue plasminogen activator, or alternatively an anti-thrombolytic agent such as an inhibitor of plasmin and plasminogen activator. The reagents added to the container along with the sample of blood promote the clot formation and then become active on the clot once it is formed to lyse the clot in a controlled and predictable manner.

A more complete appreciation of the present invention and its scope can be obtained from understanding the accompanying drawings, which are briefly summarized below, the following detailed description of presently preferred embodiments of the invention, and the appended claims.

DESCRIPTION OF DRAWINGS

FIG. 1 is a graph containing a single curve which illustrates clot formation and subsequent lysis of the clot in a single sample of whole blood or blood plasma.

FIG. 2 is a perspective view of a high sensitivity coagulation detection apparatus and a plunger sensor detection cartridge preferably used to obtain the information illustrated in FIG. 1.

FIG. 6 is a flow chart of a clot formation and clot lysis time test performed preferably using the apparatus shown in FIGS. 2 through 5.

FIG. 7 is a graph which contains a multiplicity of curves each of which is similar to the single curve shown in FIG. 1. The curves shown in FIG. 7 each represent clot formation and subsequent lysis of the clot resulting from applying varying concentrations of a thrombolytic agent to samples of whole blood or blood plasma from a single source.

FIG. 9 is a flow chart of a dose response test using thrombolytic, anti-thrombolytic, anti-fibrinolytic and other similar agents, preferably performed using the apparatus shown in FIGS. 2 through 5, to obtain the information shown in FIGS. 7 and 8.

DETAILED DESCRIPTION OF PREFERRED EMBODIMENTS

Figure 5:
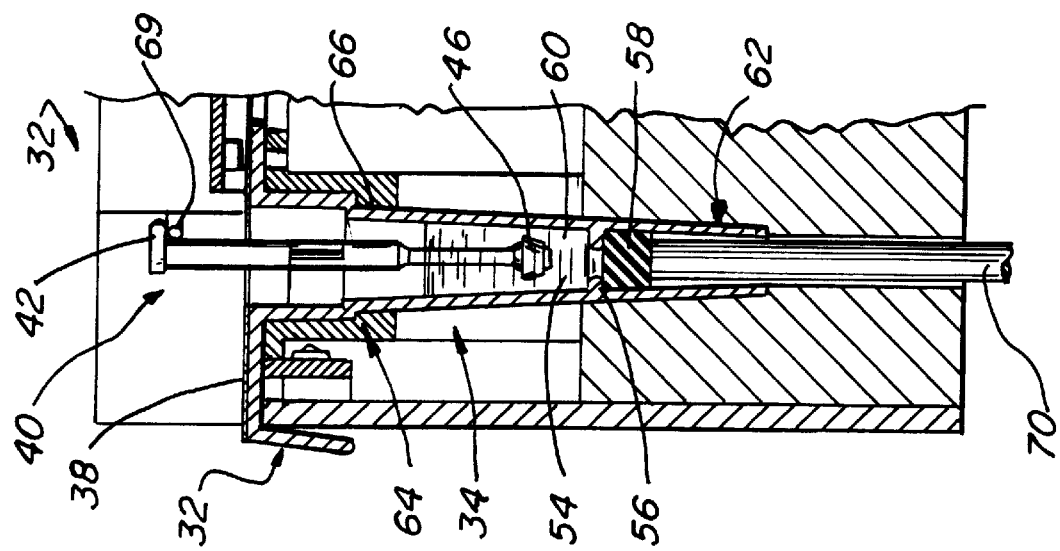
FIG. 5 is a sectional view similar to the sectional view of the cartridge shown in FIGS. 3 and 4, illustrating certain elements of the apparatus shown in FIG. 2 and the test cell of the cartridge during the course of the test involving blood clot lysis.

It has been discovered that, under conditions described below, a system which is used to monitor clot formation in a blood sample may also be used to measure clot dissolution or lysis. The term "blood" as used herein may include whole blood and the separable components thereof, such as plasma and various concentrates.

The measurement of clot lysis time following the formation of a clot in a typical blood sample is exemplified by a graph 20 shown in FIG. 1. The vertical axis indicates the time for a plunger assembly or indicator device (described in greater detail below) to descend through the mixture of the sample and reagents. This time is generally representative of the viscosity conditions of the blood sample. The horizontal axis represents the total time in seconds over which the test is run. Thus, curve 20 exemplifies clotting conditions of a sample undergoing clot formation and subsequent clot lysis as measured over a period of time sufficient to allow both clot formation and clot lysis occur.

In vivo, clot formation and subsequent clot lysis do not ordinarily transpire in a normal person absent physiological causes such as physical trauma to blood vessels, pathological blood disorders or therapeutically induced blood reactions. Similarly, under in vitro conditions, clot formation and clot lysis reactions may be absent or retarded if the medium or environment into which the blood sample is collected is made of a material which does not stimulate clot formation, such as plastic or siliconized glass. Clot formation and clot lysis reactions may also be controlled in vitro by the presence of therapeutically administered reagents. Thus, in order to accomplish in vitro measurement of blood clot formation and clot lysis as illustrated in curve 20, additional reagents have been added to the blood sample to induce or maximize clot formation and clot lysis in the mixture. These reagents preferably include heparinase, which would be added to inactivate any heparin within the blood sample that might otherwise retard the clot formation, an activating reagent such as kaolin to encourage platelet activation and promotion of clot formation, and thrombolytic or lytic agents such as streptokinase, urokinase, or recombinant tissue plasminogen activator, to promote clot lysis after clot formation.

An initial horizontal component 22 of the curve 20 is the time during which the blood sample is undergoing activities leading to clot formation. During this time, the blood sample is undergoing mixing with the reagents to form the mixture. The mixing promotes contact between blood constituents and reagents. For example, mixing can increase contact between heparinase and heparin, if present, resulting in increased inactivation of the heparin by the heparinase. Mixing also increases activation of blood constituents such as platelets by the more effective contact of the blood sample with the activating reagent. Platelet activation stimulates the platelets to release activators to further promote clot formation, among other effects. The importance of the initial mixing phase is more completely described in the present inventor's prior co-pending U.S. patent application for Platelet Activation and Function Evaluation Technique, Ser. No. 749,211, filed Aug. 23, 1991, which is assigned to the assignee hereof.

A nearly vertical component 24 of the curve 20 represents the normal, almost instantaneous increase in indicator descent time resulting from clot formation. The vertical component 24 represents changes in properties of the sample, typically a marked increase in sample viscosity. The increased viscosity primarily results from the polymerization of fibrinogen into fibrin polymers of increased molecular weight and size in the blood which occurs when the clot forms.

The next horizontal component 26 of the curve 20 indicates a time of continued measurements of maximum indicator descent time indicative of clotting prior to the commencement of measurable lytic activity. During this condition, the sample of blood remains clotted. It is during this time period that the lytic reagent becomes active on the clot which was previously formed.

A downward curving component 28 of the curve 20 represents the period during which indicator descent time is decreasing due to clot lysis and concomitant changes in properties of the sample, including a decrease in sample fluid viscosity resulting from the effectiveness of the lytic reagent. The decrease in sample fluid viscosity is due primarily to the stimulation by the lytic reagent of plasminogen and plasmin activators. The plasminogen and plasmin activators facilitate the breaking of fibrin polymer bonds, resulting in greater quantities of smaller fibrin polymer pieces.

While coagulation may be almost instantaneous as represented by the curve component 24, the more gradual nature of clot lysis, as represented by the curve component 28, reflects, in part, the accelerating nature of clot lysis. One factor which contributes to the initially slower clot lysis rate as compared to clot formation rate is the initial size of the fibrin polymers after clot formation. The relatively small surface area to volume ratio of large, unlysed fibrin polymers means that contact between the fibrin polymer surface and plasmin or other lytic agents is limited. As fibrin polymers undergo lysis, further lysis is accelerated because of an increasing exposure of new surface areas of fibrin polymers to the lytic reagents.

The final horizontal component 29 of the curve 20 represents a stabilization of the indicator descent time of the fluid sample. The indicator descent time stabilizes primarily because lysing activity has essentially ceased. The lytic activity ceases when as much of the fibrin polymers have been lysed as is reasonably possible given the particular blood sample, the reagents present, and environmental conditions such as temperature, for example. When lytic activity ceases, the viscosity of the blood sample stabilizes, and indicator descent time becomes relatively constant.

The testing that resulted in the present invention and the practical applications of the present invention are preferably achieved by the use of the assignee's plunger sensor apparatus 30 and cartridge 32 shown generally in FIGS. 2, 3, 4 and 5. Many of the details of the functionality of the apparatus 30 and the cartridge 32 have been generalized below, since the assignee's prior patents and applications disclose these details to a greater extent. See, for example, the applicant's assignee's prior U.S. Pat. Nos. 4,599,219 to Cooper, et al., and 4,752,449 to Jackson, et al., and prior U.S. application Ser. No. 644,007 to Smith, filed Jan. 11, 1991.

In general, the cartridge 32, as shown in FIGS. 2, 3, 4 and 5 includes a plurality of test cells 34, each of which is formed generally as a downward extending truncated tube-like member 36. Each of the tube-like members 36 is connected to an upper shelf portion 38. A plunger assembly 40 extends downward from an upper open end of each test cell 34 into the tube-like member 36. Each plunger assembly 40 includes at least one and preferably a pair of flags 42 at its upper end located at a position above the shelf portion 38. The plunger assembly 40 also includes a shaft which extends from the flags 42 downward to a lower end 46 upon which a disk member 48 is attached. The disk member 48 is formed of resilient material and includes an annular flange 50 located above and extending outward from a generally cylindrical main body portion 52. The annular flange 50 includes slots or openings (not shown) formed therein at outer circumferential locations. The plunger assembly 40 functions as the indicator device to determine the clotting conditions of the sample when the cartridge 32 is used with the apparatus 30.

Figure 3:
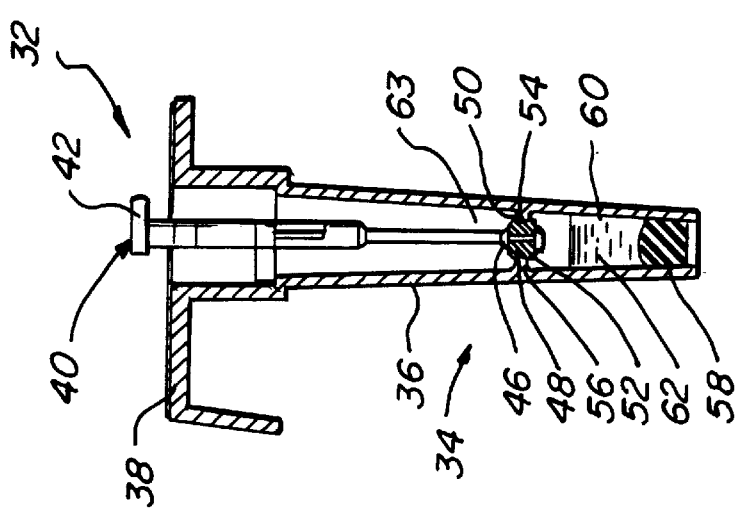
FIG. 3 is a vertical section view of a test cell of the cartridge shown in FIG. 2, taken substantially in the plane of line 3—3.

As shown in FIG. 3, prior to using the plunger sensor cartridge 32 in the apparatus 30, the disk member 48 is positioned with its main body portion 52 located in and sealed against an opening 54 formed by a partition 56 extending inwardly from the tube-like member 36. The partition 56 is located between the upper and lower open ends of the tube-like member 36. A resilient flexible plug 58 is positioned in the interior of the tube-like member 36 at its lower open end. The plug 58 seals against the inner side walls of the tube-like member 36 and confines a quantity of one or more reagents 60 in a reagent chamber 62 between the partition 56 and the plug. The reagents 60 may be a liquid or a solid powder. When more than one reagent 60 is confined in the chamber 62, the reagents are selected to co-exist with one another without adverse influence on the properties of other reagents. A reaction chamber 63 is generally defined by that portion of the open tube-like member 36 above the partition 56.

Figure 4:
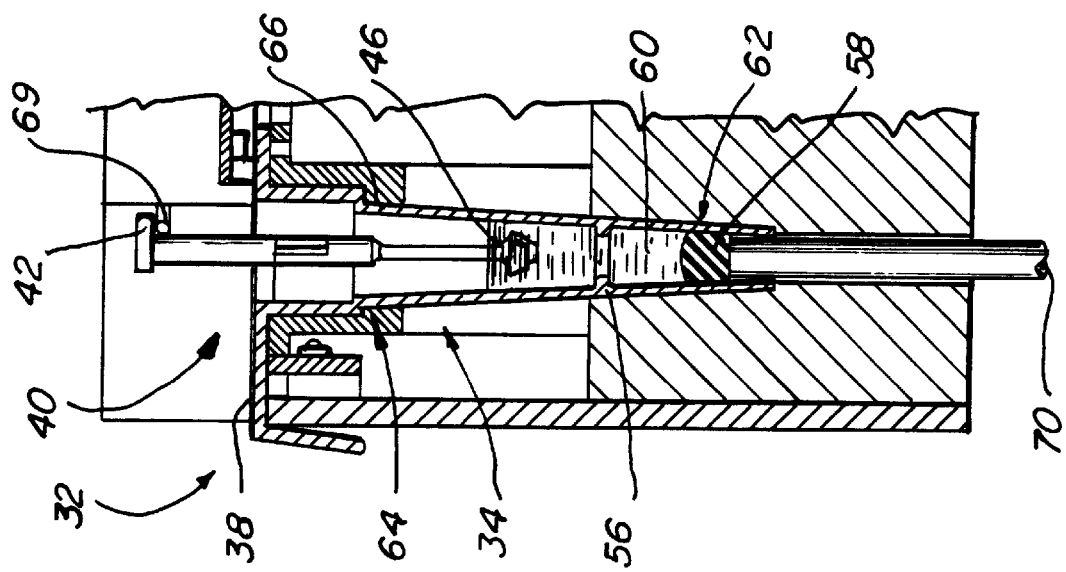
FIG. 4 is an enlarged sectional view similar to the sectional view of the cartridge shown in FIG. 3, illustrating certain elements of the apparatus shown in FIG. 2 and the test cell of the cartridge at the commencement of the test involving blood clot lysis.

The plunger sensor cartridge 32 is inserted into a receiving block 64 in the apparatus 30 during use, as is shown in FIGS. 2, 4 and 5. Each of the test cells 34 extends into a receptacle 66 of the receiving block 64. Each receptacle 66 has a configuration adapted to receive a test cell 34, while the shelf portion 38 of the cartridge 32 sits on top of the block 64.

The apparatus 30 is generally formed of subassemblies. A plunger lifting subassembly (not fully shown), which includes a lift wire 69 (FIGS. 4 and 5), initially lifts the plunger assembly 40 from its seated position (shown in FIG. 2) and thereafter, lowers and releases the plunger assembly 40 and allows it to descend through the liquid mixture in the reaction chamber. The lift wire 69 and the plunger lifting subassembly control the lifting movement of the plunger assembly. A reagent drive subassembly (not shown), which includes a plug driver shaft 70, moves the plug 58 to force the reagent 60 into the reaction chamber 63 after the plunger assembly 40 has been removed from its seated position. A dispensing subassembly 72 (FIG. 2) automatically supplies a sample of blood into the reaction chamber 63 of each test cell 34 of the cartridge 32 before the test and prior to the initial movement of the plunger assembly 40 from its seated position. An optical sensing system (not shown) senses the physical descent of the plunger assembly 40 through the mixture in the reaction chamber 63 in order to detect coagulation and lytic conditions.

The sample of blood is supplied by the dispensing subassembly 72 to the reaction chamber 63 from a syringe 74 having a blunt needle 76 attached thereto, as shown in FIG. 2. The syringe 74 is manually attached to the dispensing subassembly 72 of the apparatus 30 by a retention device 77. The chamber of the syringe 74 contains blood, preferably fresh drawn from the patient, upon which the lysis testing is to be performed. Of course, prior to attachment of the syringe 74 to the dispensing subassembly 72, all air and other voids in the fluid within the syringe chamber and the blunt needle 76 are removed in a conventional manner. A plunger 78 located within the chamber of the syringe 74 is engaged with a drive wheel 80. Rotation of the drive wheel 80 forces the syringe plunger 78 downward a predetermined amount and thereby expels a predetermined amount of blood from the lower end of the blunt needle 76. The extent to which the syringe plunger 78 is moved downward determines the quantity of fluid expelled from the needle 76.

The dispensing subassembly 72 also includes a movement frame 84 which is moved laterally in the horizontal direction along guide rods 86. The degree of lateral movement is controlled by rotation of a threaded shaft 88 by a microprocessor-controlled motor (not shown) in accordance with programmed information, thereby locating the blunt needle 76 directly above the open upward end of each test cell 34 of the cartridge 32. After attaining the proper lateral location, the movement frame 84 moves the syringe 74 vertically downward to insert the lower end of the blunt needle 76 into the upper open end of each of the test cells 34.

The desired amount of fluid sample is automatically dispensed into the reaction chamber 63 of the test cell 34. Thereafter, the blunt needle 76 is withdrawn from the test cell 34 by the dispensing subassembly 72 and is moved to the next lateral position over a test cell 34. The sequence again repeats itself, resulting in that predetermined amount of blood sample needed and desired for conducting the particular clot lysis test being dispensed into the reaction chamber 63 of each test cell 34 of the cartridge 32.

As shown in FIGS. 3, 4 and 5, the lift wire 69 of the plunger lifting subassembly is initially positioned in a lowermost location, and in that position a horizontal segment of the lift wire fits underneath the flags 42 of the plunger assembly 40. Upward movement of the lift wire 69 lifts each plunger assembly 40 upward, thereby removing the disk member 48 from its seated, sealed location in the opening 54 of the partition 56, of each tube-like member 36 as is shown in FIG. 4. A fluid communication passageway through the opening 54 between the reagent chamber 62 and the reaction chamber 63 is thereby established. Thereafter, or simultaneously with the upward movement of the plunger assembly 40, one of the plurality of plug driver shafts 70 of the reagent drive subassembly moves upward, forcing each plug 58 upward, collapsing the reagent chamber 62 and forcing its contents 60 into the reaction chamber 63. The reagent 60 is thereafter mixed with the fluid sample in the reaction chamber 63 by reciprocating the plunger assembly 40. This condition is illustrated in FIG. 5.

Since the tube-like member 36 of each test cell 34 is formed of clear material such as plastic, optical sensors (not shown), which are located within the interior of each receptacle 66 of the receiving block 64, are used for the purpose of monitoring the descent of the plunger assembly 40 relative to the controlled descent or movement of the lift wire 69. In this way, the time which is required for the plunger assembly 40 to descend through the mixture in the reaction chamber 63 is measured during the performance of the tests of the present invention.

A flow chart of a preferred form of a clot lysis test 100 is shown in FIG. 6 and will be described as performed in conjunction with the apparatus 30 and cartridge 32 as shown in FIGS. 2, 3, 4 and 5. The steps in the clot lysis test 100 will be referred to below by reference numbers enclosed in parentheses. The plunger sensor cartridge 32 is first inserted (102) into the apparatus 30 into the receptacles 66 of receiving block 64 of the apparatus 30. The syringe 74 which has been previously filled with the blood sample to be tested is then inserted (104) into the sample dispensing subassembly 72 of the apparatus 30. The operator enters any required information utilizing a plurality of control switches 95 (FIG. 2) on the exterior housing of the apparatus 30 and begins the test 100 by activating one of. the control switches. A precise predetermined amount of blood is then injected (106) into the reaction chamber 63 of the cell 34 of the cartridge 32, preferably by the dispensing subassembly 72. The blood sample in the reaction chamber 63 is initially kept separate from the reagents 60 in the reagent chamber 62, until the plunger lifting subassembly lifts the plunger assembly 40 and the reagent drive subassembly 70 forces the plug 58 upward, thereby adding the reagents (108) into the reaction chamber 63 and creating a test mixture of the blood sample and the reagent. In this manner, the blood sample in the reaction chamber 63 is kept separate from an activating reagent 60 in the reagent chamber 62 until the commencement of the test thereby insuring that coagulation and lysis will be consistently measured from a predetermined starting point.

The plunger lifting subassembly lifts the plunger assembly 40 and allows it to descend on a repeating basis, thereby reciprocating the plunger assembly (109), to achieve initial mixing of the blood sample and the reagents. This initial mixing phase has been determined to be important in obtaining precise activated clotting time data, as is described in the aforementioned co-pending application, Ser. No. 749,211. At a predetermined point in time after the mixing phase is commenced, the clot formation and lysis phase of the test occurs. The clot formation and lysis phase may or may not begin after the mixing phase is completed, but the clot formation and lysis phase should begin under predetermined repeatable conditions, as explained more completely in the co-pending application Ser. No. 644,007. The clot formation and lysis will be measured (110) from this point in time.

Upon test commencement, the plunger assembly 40 is reciprocated (112) by the plunger lifting subassembly lifting the plunger assembly and allowing it to descend. The time taken for the plunger to descend through the mixture is measured (114) by the optical sensing system. The plunger descent time relates to and is used for detecting the physical condition (viscosity) of the sample. The sequence of reciprocating the plunger assembly 40 (112) and measuring the plunger descent time (114) is repeated. Preferably, the descent time measurement of each plunger reciprocation is maintained in the memory of the microprocessor or otherwise recorded for subsequent calculations and possible data display purposes, and it is by comparing previous descent times with one or more currently measured descent times that coagulation and lysis conditions are determined.

As the viscosity of the test mixture changes due to clotting, the descent of the plunger assembly 40 relative to the lowering movement of the lift wire 69 decreases. Once a change in the descent of a predetermined magnitude is detected (116), coagulation of the sample is determined to have occurred. Coagulation is exemplified by component 24 of the curve 20 shown in FIG. 1. The point in time at which coagulation has been determined to occur is noted and the coagulation time is computed (118). The steps 109, 110, 112, 114, 116 and 118 measure coagulation, and are referred to below as a clotting phase 139.

After clotting occurs, the plunger lifting subassembly continues to reciprocate (120) the plunger assembly 40 and plunger descent time is continued to be measured (122) while the blood in the mixture is coagulated. This is exemplified by the component 26 of the curve 20 shown in FIG. 1. Any lysing agents present in the blood or lysing reagents 60 previously added to the blood become effective once the clotting has occurred, which is represented by the component 26 shown in FIG. 1. After the lysing agents and reagents begin to cause lysis of the clot, the viscosity of the test mixture begins to change and the descent time of the plunger assembly 40 begins to decrease as the lysing agents and reagents become more and more effective on the clot. This condition is exemplified by component 28 of the curve 20 shown in FIG. 1.

Once a change of a predetermined magnitude in the plunger descent time is detected, the time is noted and lysis is determined to have started. The reciprocation of the plunger continues (126), and the descent time is measured (128). Once it is determined that changes in plunger descent time are minimal or no longer occurring (component 29 of the curve 20 in FIG. 1), the time is noted and lysis of the coagulated blood sample is determined to have been completed (130). There are a variety of ways to determine whether changes are minimal or no longer occurring, such as calculating the slope of the component 28 of curve 20 in FIG. 1 and determining whether it has reached a predetermined value.

Upon detection of completed lysis (130) the lysis time is computed (132). The lysis time may computed in a number of ways, such as the time from the detection of coagulation (116) through the detection of the completed lysis event (130), from the commencement of timing (110) to a predetermined endpoint after lysis, from the detection of clotting (116) to start of lysing (124), or from start of lysing to end of lysing (curve segment 28, FIG. 1). Which ever way the lysis time is computed, in the preferred embodiment the lysis time is calculated rapidly due to microprocessor control of the computation. The steps 120, 122, 124, 126, 128, 130 and 132 constitute a lysis phase 138, during which the lysis event occurs.

In the preferred form of the coagulation and clot lysis test 100 the coagulation and lysis times are displayed on a display 96 on the outside housing of the apparatus 30 (FIG. 2). After completing the test, the operator removes the syringe 74 (134) and cartridge 32 (136).

By measuring the lysis time of a blood sample immediately after measuring the coagulation time of the blood sample in this manner, coagulation and lysis times can be compared without concern that changes in environmental conditions between the two tests might make a comparison less meaningful. As is clear from the description of the apparatus 30, cartridge 32 and the coagulation and lysis test 100, operator intervention is limited to operations occurring before the clotting phase 139 and after the lysis phase 138, thus maximizing the consistency of coagulation and lysis measurements. Further, by forming the clot and measuring the lysis of the clot in a continuum of steps in a single test 100, the opportunities for error and inconsistency are minimized compared to those tests which require the formation of a clot separately from the execution of the lysis test.

Performing the test 100. on a sample of blood measures sequentially clotting and lytic activity in the sample of blood. The lytic activity measured by the test 100 is that caused by both the natural fibrinolytic activity of the blood and therapeutically induced thrombolysis. To accurately monitor changes in blood viscosity and other properties of blood caused by lytic activity and to distinguish changes caused by lytic activity from changes caused by other chemical agents or physiological processes, lytic activity must be suppressed. One way in which lytic activity can be suppressed is by the addition of an inhibitor of plasmin and plasminogen activators such as 6-amino-caproic acid. Inhibitors of plasmin and plasminogen activators deactivate naturally occurring and therapeutically administered lytic agents which would otherwise promote clot lysis. By deactivating these lytic agents, all changes in properties of clotted blood subsequently measured will result other than from lytic activity.

A preferred form of a test to monitor total lytic activity which uses 6-amino-caproic acid is performed on a sample of blood from an individual with a plunger technique apparatus 30 and cartridge 32 and utilizes the test sequence 100 shown in FIG. 6. In the preferred embodiment of the test to monitor lytic activity, a deactivator of anticoagulants, for example, an inhibitor of heparin such as heparinase in a presently preferred amount of ten IU, is placed in the reaction chamber 63 of each of a plurality of test cells 34 of a cartridge 32. The heparinase will be effective to disable any heparin in the blood samples which will be subsequently injected into the reaction chambers. An inhibitor of plasmin and plasminogen activators is added to the reagent chamber 62 of one test cell 34 of the cartridge 32 used in this test. No inhibitor of plasmin and plasminogen activators is added to the reagent chamber 62 of at least one other test cell 34 of the cartridge 32. Blood samples from a single larger blood sample are then injected into the test cells 34 by the dispensing subassembly 72 of the apparatus 30. In the preferred form of the test, the clotting and the subsequent lysis phases for the blood contained in the test cells 34 are detected and measured as shown by phases 139 and 138 of the test 100 illustrated by FIG. 6. At the conclusion of the measuring of the coagulation and lysis events in the test cells 34, calculations are performed. The lysis time calculated for the test cell in which an inhibitor of plasmin and plasminogen activators has been added represents changes in properties of the clotted blood caused by other than lytic activity. The lysis time of the blood sample in the cell 34 in which no inhibitor is added represents clot lysis caused by both natural fibrinolytic activity and any thrombolytic agents present in the blood sample. The lysis times of the two blood samples are then compared.

If there is no statistically significant difference in the lysis times, such that the lysis time of the blood sample to which no inhibitor of plasmin and plasminogen activators has been added is approximately the same as the lysis time of the sample to which an inhibitor has been added, and the lysis times are abnormally long, then pathological fibrinolysis, an absence of thrombolytic agents or the presence of therapeutically administered anti-thrombolytic agents may be indicated. If there is a statistically significant difference in the lysis times of the test cells 34, such that the lysis time of the blood sample to which no inhibitor of plasmin and plasminogen activators has been added is significantly shorter than the lysis time of the sample to which an inhibitor has been added, the contribution to changes in properties of the blood caused by lytic activity can be determined and the results of the test for monitoring total lytic activity may be presented. For example, the display 96 on the face of the apparatus 30 may present the time differential between the lysis time of the blood sample in which an inhibitor of plasmin and plasminogen activators was added and the lysis time of the blood sample to which no such inhibitor was added. Alternatively, a mathematical relationship, such as a ratio, of this information might be provided.

The present invention also involves a test to detect the lytic effect of an administration of a predetermined dose of a thrombolytic agent or an anti-thrombolytic agent. As used herein, the term anti-thrombolytic agent includes both anti-thrombolytic and anti-fibrinolytic agents. This lytic dose response test may also be performed with the apparatus 30 and cartridge 32. The preferred form of the lytic dose response test utilizes the lysis phase 138 of the test 100 shown in FIG. 6. The lytic dose response test may be performed on a blood sample for which a clot forming test has been performed immediately preceding the lytic dose response test, or the lytic dose response test may be performed on a sample of previously clotted blood, which clot was pre-formed outside the test cell 34.

Figure 8:
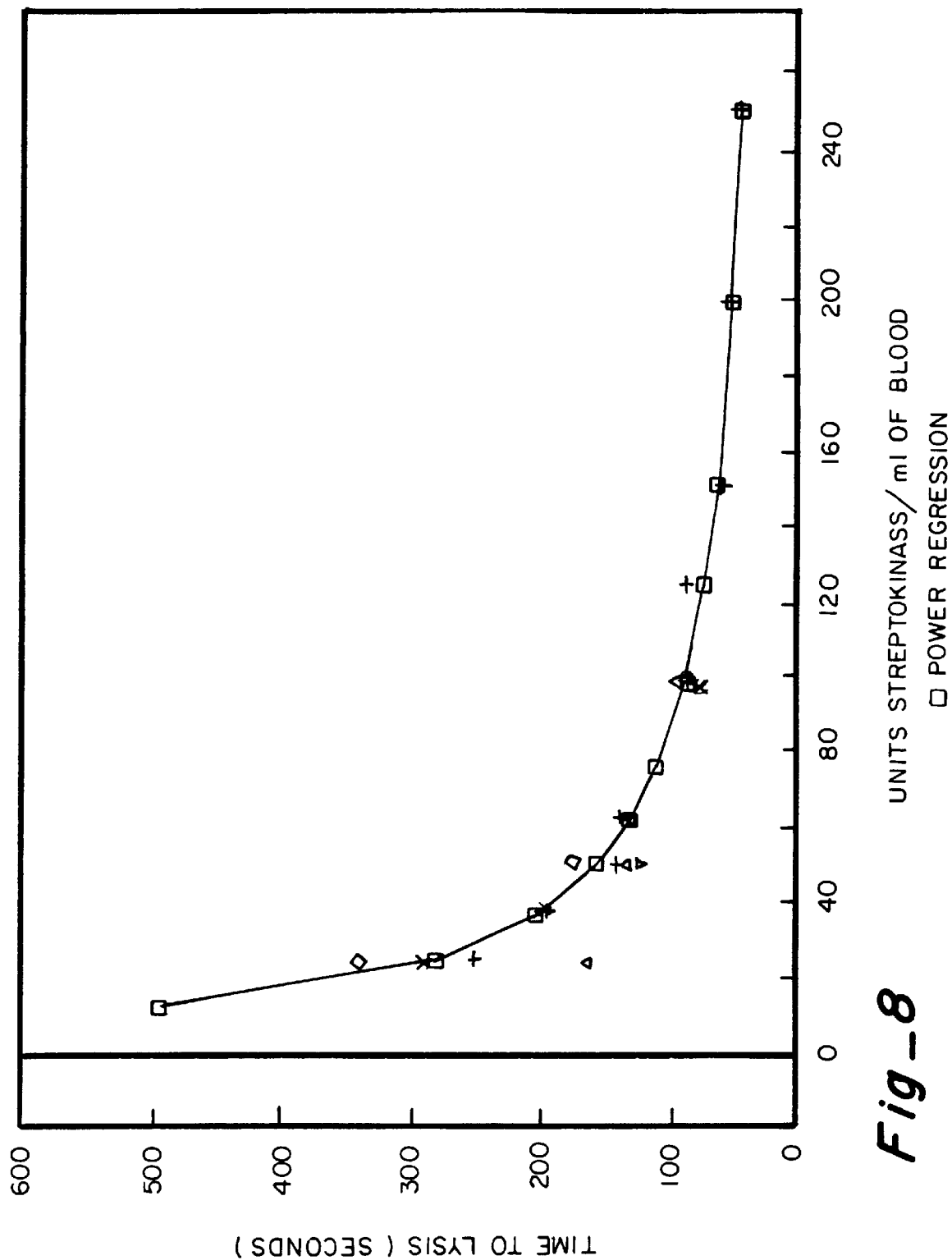
FIG. 8 is a graph containing a single curve which illustrates the typical lysis response to varying concentrations of thrombolytic agents, based on the information available from the curves shown in FIG. 7.

FIGS. 7 and 8 illustrate the results achieved by performing a lytic dose response test. Each of the multiplicity of traces 141, 142, 143, 144, 145, and 146 of graph 140 shown in FIG. 7 represents the blood clot formation and the subsequent clot lysis on different samples of the individual's blood which have been mixed with different concentrations of the thrombolytic or anti-thrombolytic agent. Each of the traces 141–146 is therefore similar to the single trace 20 shown in FIG. 1. Each of the steps of the clotting phase 139 and lysis phase 138 of the test 100 described and illustrated in FIG. 6 are performed to obtain the information pertinent to each of the traces 141–146.

To obtain the information represented by the traces 141–146, at least one cartridge 32 containing a multiplicity of test cells 34 is used. The reagent chambers 62 of the cells 34 of the cartridge 32 each contain different predetermined amounts of the thrombolytic or anti-thrombolytic agent calculated to correspond to predetermined concentrations of the particular agent to be administered in vivo. The reagent chamber 62 of one test cell 34 of the cartridge 32 contains no thrombolytic or anti-thrombolytic agent. The test cell 34 to which no thrombolytic or anti-thrombolytic agent has been added is referred hereafter as the control cell. If one cartridge contains an insufficient number of test cells, two or more cartridges can be employed. Of course different amounts of the thrombolytic or anti-thrombolytic agent will be present in each of the test cells collectively, and the information obtained by conducting the separate tests is integrated into a single graph shown in FIGS. 7 and 8.

The clotting phase 139 and lysis phase 138 of the test 100 (FIG. 6) are conducted on the blood samples in each test cell 34 and in the control cell. When lysis of all the test cells 34 has been detected as complete or it has been determined that a predetermined time has elapsed without lysis occurring, timing stops. The lysis time is then calculated for each test cell 34 and the control cell.

The traces of the graph 140 shown in FIG. 7 each represent graphically the coagulation and lysis of the blood samples of each test cell 34 and of the control cell, obtained by conducting a test 100 (FIG. 6) on each blood sample. While the traces of the graph 140 shown in FIG. 7 where obtained by conducting a test 100 in the presence of a thrombolytic agent and will be discussed herein with respect to the thrombolytic agent, a dose response graph may also be obtained by performing a test 100 in the presence of an anti-thrombolytic agent. Trace 141 of the graph 140 represents the clotting and lysis conditions of the blood sample in the control cell to which no thrombolytic or anti-thrombolytic agent was added. Without some pathological or therapeutically induced condition being present in the individual whose blood sample is being tested, clot lysis may not occur within a predetermined time period in the control cell containing no thrombolytic agent. However, in the test cells 34 to which the different concentrations of the thrombolytic reagent have been added, clot lysis does occur. Traces 142, 143, 144 or 145 each have a vertical component analogous to component 28 shown in FIG. 1, indicating the time when lysis has taken place. For those blood samples mixed with higher concentrations of the thrombolytic agent, clot lysis generally occurs sooner. For example trace 142 indicates that a high concentration of thrombolytic agent was mixed with the blood sample upon which that test was conducted, but trace 145 indicates that the concentration of the thrombolytic agent is low, resulting in a greater clot lysis time.

Preferably, the reagent used in the cartridge for the lytic dose response test for a thrombolytic agent is streptokinase. However other thrombolytic agents, such as urokinase and recombinant tissue plasminogen activator may also be used. The concentrations of streptokinase per milliliter of whole blood represented by the traces 141, 142, 143, 144 and 145 of the graph 140 are 0, 100 IU, 80 IU, 60 IU, 40 IU, and 20 IU, respectively. In the case of streptokinase, the range of from 0 to 100 IU per milliliter whole blood is used because the range broadly brackets 60 IU streptokinase which is generally regarded to be a desired concentration of streptokinase for in vivo treatment.

A dose response test for anti-thrombolytic effects is similar. Different concentrations of the anti-thrombolytic agent are placed in each test cell with a sample of blood which contains an amount of previously administered thrombolytic agent, usually during therapy. The control cell is also employed to obtain data as to the thrombolytic response of the blood sample free of influence from the anti-thrombolytic agent. The tests are run in a similar manner and data and graphs are obtained. The data and graphs describe the response of the blood which was previously treated with a thrombolytic agent, to varying doses of an anti-thrombolytic agent. This data is useful in more precisely establishing the dose of an anti-thrombolytic agent to administer to a particular patient to reverse or partially reverse the thrombolytic effect of the blood which has previously been treated with a thrombolytic agent.

When thrombolytic agents other than streptokinase, or when anti-thrombolytic agents are used, the range of concentrations of the other thrombolytic or anti-thrombolytic agents used in lytic dose response cartridges should be varied so as to encompass and bracket the desired concentration to be administered in vivo.

The lysis times obtained from the lytic dose response test represent the unique response of an individual to various doses or concentrations of the thrombolytic or anti-thrombolytic agent. This data may be combined in a single curve, for example, that shown in FIG. 8 for a thrombolytic agent, to more precisely predict the in vitro response of the individual to a specific administered dose of thrombolytic or anti-thrombolytic agent, or to determine the quantity of the dose to administer to achieve a specific lytic response.

FIG. 8 graphically represents the combined results of all of the dose response tests previously described and illustrated in FIG. 7, in a single curve 150. The vertical axis of the graph of FIG. 8 represents the measured lysis times. The horizontal axis of the graph of FIG. 8 represents the different concentrations of the thrombolytic agent in terms of units of the thrombolytic agent (streptokinase) per volume of blood. The information on the horizontal axis of FIG. 8 may be extrapolated to account for any differences resulting from in vivo administration compared to the response to the in vitro concentration of the thrombolytic agent on the blood sample contained in each test cell.

The individual data points from each of the tests performed on the samples in the lytic dose response cartridge(s) are points describing the curve 150. The curve 150 is derived from the individual data points by known curve fitting or derivation techniques. The curve may be derived by the microprocessor of the apparatus 30, or by means or techniques external to the apparatus. After the dose response curve 150 has been calculated, an equation may be derived which mathematically represents lysis time as a function of the concentration of thrombolytic dose administered. The curve 150 or the equation which represents the dose response curve 150, may be displayed on the display 96 on the housing of the apparatus 30. In the alternative, the equation, graph or data information may be retained internally in the microprocessor to be used as a basis for calculating the desired dose to administer to achieve a specific lytic response in an individual, based on information which the user supplies from the control keys or switches 95 (FIG. 2).

Further still, future testing may reveal such substantial similarities in a large number of individual dose response curves. If so, a more generic dose response curve, applicable to a statistically significant proportion of the general population, might be programmed into the microprocessor of the apparatus. Such a generic dose response curve could be used to determine doses to be administered without resort to actually determining the individual dose response curve. In the case of a pre-programmed generic dose response curve, a reduced number of individual dose response tests might be used to prove or disprove the validity of the generic curve, without the necessity of running a complete number of dose response tests to completely construct a unique dose response curve. In addition, some of the tests described above could be employed to determine the effectiveness of a dose of thrombolytic or anti-thrombolytic agent administered based on the generic dose response curve. Further still, the generic dose response curve might be employed to select a lytic dose response cartridge having a predetermined range of concentrations by which to evaluate an individual dose response over a limited segment of the individual dose response curve which is of particular interest. This feature is of particular utility in a "target" lytic dose response described below.

As a result of the lytic dose response features of the present invention, a target dose response test 160, illustrated in FIG. 9, is available to predict the dose of a thrombolytic or anti-thrombolytic agent to administer in order to obtain a predetermined or selected "target" lysis time. In the preferred embodiment of this test 160, the operator first inserts a cartridge 32 (162) containing a multiplicity of cells 34 into the apparatus 30. One of the cells 34 is the control cell previously described, while the other of the plurality of cells contain various amounts of a thrombolytic or anti-thrombolytic agent, also previously described. The operator then enters via touch sensitive switches 95, a desired fibrinolytic response time (164), hereinafter referred to as a target lysis time. After a predetermined period of time, if no such target lysis time is supplied by the operator (168), then a predetermined standard "default" target lysis time is then set by the apparatus (170), for example, 120 seconds. Once the target lysis time is set, a syringe of blood is inserted (172). The clotting phase 139 and the subsequent clot lysis phase 138 are then performed on the blood samples in each test cell of the cartridge. The phases 138 and 139 have previously been described and illustrated in the test 100 shown in FIG. 6. After lysis has occurred in each test cell 34 or it is determined that a predetermined time has elapsed without lysis occurring, then lysis times of each of the plurality of test cells 34 is calculated (178). As described previously, a dose response curve is calculated (180) for the range of concentrations of thrombolytic or anti-thrombolytic agent employed in the cartridge. Based upon the dose response curve, the dosage of the thrombolytic or anti-thrombolytic agent is then calculated which is predicted to yield the target lysis time (182). In the preferred embodiment, the specific dose response calculated to yield the target lysis time is displayed (184) on the display 96 of the outside housing of the apparatus 30. Thereafter, the syringe 74 may be removed (186) and the cartridge 32 also removed (186).

From the foregoing description, it can be appreciated that various clot lysis conditions may be measured by measuring clot formation and clot lysis in sequential manner. Furthermore, utilization of the apparatus 30 in conjunction with a cartridge 32 and test cells 34 to sequentially measure coagulation and lysis of a sample of blood requires a minimum of operator intervention and results in accurate and highly sensitive coagulation and lysis measurements which are quickly derived. Adding various reagents such as inhibitors of plasminogen and plasminogen activators to the test cells achieves the ability to accurately monitor total lytic activity in the blood and to distinguish changes to blood contributed by other than a natural fibrinolytic response or thrombolytic agents. Additionally, by adding various reagents such as thrombolytic, anti-thrombolytic and anti-fibrinolytic agents to the test cells in predetermined concentrations, dose responses to thrombolytic and other agents can also be determined. Moreover, the utilization of the dose response tests in conjunction with the selection of target dose response as described herein, can provide physicians with dosage guidance heretofore unavailable. By utilizing the apparatus, cartridge and test cells, all of the tests described can be conducted reliably, accurately, quickly and sensitively.

Presently preferred embodiments of the present invention and many of its improvements have been described with a degree of a particularity. It should be understood that this description has been made by way of preferred example, and that the invention is defined by the scope of the following claims.

What is claimed:

1. A method of evaluating a clot lysis condition by measuring lytic activity in blood, comprising the steps of:
   mixing a blood sample with a reagent to induce formation of a clot in the sample of blood;
   continuously evaluating a property of the sample of blood from before a first time when the clot is detected until a second time when lysis of the clot is detected;
   detecting said first time at which said clot forms;
   detecting said second time at which said clot lyses;
   measuring an elapsed time period from said first time at which said clot forms to said second time at which said clot is lysed; and
   comparing said elapsed time period with a normal lytic response time to evaluate the clot lysis condition in the sample of blood.

2. A method as defined in claim 1 further comprising:
   adding the sample of blood to a container; and
   performing the steps of mixing the sample of blood and continuously evaluating a property of the sample of blood in the container.

3. A method as defined in claim 2 further comprising:
   mixing the sample of blood in the container with at least one reagent which functions to promote one of clot formation or clot lysis, prior to commencing the clot forming step.

4. A method as defined in claim 3 wherein the reagent comprises a clot activating agent.

5. A method as defined in claim 4 wherein the clot activating agent is kaolin.

6. A method as defined in claim 3 wherein the reagent comprises a thrombolytic agent.

7. A method as defined in claim 6 wherein the thrombolytic agent is streptokinase, urokinase or recombinant tissue plasminogen activator.

8. A method as defined in claim 3 wherein the reagent comprises an inhibitor of plasmin and plasminogen activators.

9. A method as defined in claim 8 wherein the inhibitor of plasmin and plasminogen activators is 6-amino-caproic acid.

10. A method as defined in claim 3 wherein the reagent comprises an agent for deactivating any anticoagulant present in the sample of blood.

11. A method as defined in claim 10 wherein the anticoagulant deactivator is an inhibitor of heparin.

12. A method as defined in claim 11 wherein the inhibitor of heparin is heparinase.

13. A method as defined in claim 3 further comprising:
   mixing a plurality of reagents with the sample of blood, the plurality of reagents including an agent for deactivating any anticoagulant present in the sample of blood and an agent for activating clotting of the sample of blood.

14. A method as defined in claim 13 wherein the plurality of reagents further includes a thrombolytic agent for initiating lysis in the sample of blood.

15. A method as defined in claim 1 wherein the clot lysis condition is the total lytic activity, and said method further comprises the steps of:
   mixing in a first container a first sample of the blood with a first agent for deactivating any anticoagulant present in the first sample and a second agent for activating clotting of the first sample;
   mixing in a second container a second sample of the blood with a first agent for deactivating any anticoagulant present in the second sample, a second agent for activating clotting of the second sample, and a third agent for inhibiting plasmin and plasminogen activators in the second sample;
   performing the clot formation, clot detection, clot lysing, measuring and evaluating steps separately on each of the first and second samples;
   comparing the clot lysis time of the first sample with the clot lysis time of the second sample; and
   determining the total lytic activity by any significant difference in the clot lysis times of the first and second samples.

16. A method as defined in claim 15 wherein the first agent for deactivating any anticoagulant present in the first sample and the first agent for deactivating any anticoagulant present in the second sample are inhibitors of heparin.

17. A method as defined in claim 16 wherein the inhibitor of heparin is heparinase.

18. A method as defined in claim 15 wherein the second agent for activating clotting of the first sample and the second agent for activating clotting of the second sample are kaolin.

19. A method as defined in claim 15 wherein the third agent for inhibiting plasmin and plasminogen activators in the second sample is 6-amino-caproic acid.

20. A method as defined in claim 1 wherein the clot lysis condition is a dose response to a thrombolytic agent, said method further comprising the steps of:
   mixing in a first container a first sample of the blood with a first predetermined amount of the thrombolytic agent;
   mixing in a second container a second sample of the blood with a second predetermined amount of the thrombolytic agent;
   creating different concentrations of the thrombolytic agent in the first and second samples by adjusting the quantities of the thrombolytic agent mixed in the first and second samples relative to the quantities of blood in the first and second samples;
   performing the steps of mixing, continuously evaluating, detecting, measuring, and comparing separately on each of the first and second samples after the different concentrations have been established; and
   utilizing the measured clot lysis times from the first and second samples to determine the response of the blood to different concentrations of the thrombolytic agent.

21. A method as defined in claim 20 wherein the step of utilizing the measured clot lysis times of the samples to determine the response of the blood to different concentrations of the thrombolytic agent further comprises:

deriving a mathematical expression which describes the relationship between the measured clot lysis times and the concentrations of the thrombolytic agent in the samples.

22. A method as defined in claim 21, said method further comprising:

choosing a target lysis time; and predicting a concentration of the thrombolytic agent to yield the target lysis time by application of the mathematical expression.

23. A method as defined in claim 1 wherein the clot lysis condition is a dose response to an anti-thrombolytic agent, said method further comprising the steps of:

mixing in a first container a first sample of the blood with a first predetermined amount of the anti-thrombolytic agent;

mixing in a second container a second sample of the blood with a second predetermined amount of the anti-thrombolytic agent;

creating different concentrations of the anti-thrombolytic agent in the first and second samples by adjusting the quantities of the anti-thrombolytic agent mixed in the first and second samples relative to the quantities of blood in the first and second samples;

performing the steps of mixing, continuously evaluating, detecting, measuring, and comparing separately on each of the first and second samples after the different concentrations have been established; and utilizing the measured clot lysis times from the first and second samples to determine the response of the blood to different concentrations of the anti-thrombolytic agent.

24. A method as defined in claim 23 wherein the step of utilizing measured the clot lysis times of the samples to determine the response of the blood to different concentrations of the anti-thrombolytic agent further comprises:

deriving a mathematical expression which describes the relationship between the measured clot lysis times and the concentrations of the anti-thrombolytic agent in the samples.

25. A method as defined in claim 24, said method further comprising:

choosing a target lysis time; and predicting a concentration of the anti-thrombolytic agent to yield the target lysis time by application of the mathematical expression.

26. A method as defined in claim 1 wherein the measuring step comprises:

placing an indicator device in the sample;

reciprocatively moving the indicator device in the sample;

repeatedly allowing the indicator device to descend through the sample during each reciprocation;

measuring the descent of the indicator device through the sample;

measuring the time taken for an increase in descent time of the indicator device to occur upon forming of the clot; and subsequently measuring the time taken for a decrease in descent time of the indicator device to occur upon lysing of the clot.

27. A method as defined in claim 26 wherein the indicator device is a plunger; the sample is added to a container; the container is a test cell; the test cell comprises a reagent chamber, a reaction chamber, and a displaceable sealing member connected to the indicator device and initially positioned between the reagent and reaction chambers; and the steps of the clot lysis condition test are performed in the reaction chamber.

28. A test cell, in which to perform a clot lysis condition test, said test cell comprising:

a reagent chamber containing a clot activating agent and one of a thrombolytic or anti-thrombolytic agent;

a reaction chamber; and a displaceable sealing member between the reagent and reaction chambers.

29. A method as defined in claim 28, wherein the first change in the property of the sample of blood is an increase in viscosity, and wherein the second change in the property of the sample of blood is a decrease in viscosity.

30. A method of evaluating a clot lysis condition in blood, comprising the steps of:

mixing a blood sample with a reagent to induce formation of a clot in the sample of blood;

continuously evaluating a property of the sample of blood from a predetermined time before the formation of the clot is detected until lysis of the clot is detected;

detecting a first time at which said clot forms, wherein said first time is detected by a first change in the property of the sample;

detecting a second time at which said clot lyses, wherein said second time is detected by a second change in the property of the sample;

measuring a clot formation time period from said predetermined time to said first time at which said clot is formed;

measuring a clot lysis time period from said predetermined time to said second time at which said clot is lysed; and comparing said clot formation and clot lysis times to evaluate the clot lysis condition in the blood.

31. A method as defined in claim 30, wherein the first change in the property of the sample of blood is an increase in viscosity, and wherein the second change in the property of the sample of blood is a decrease in viscosity.

* * * * *